US012714325B2

(12) United States Patent
Sohlden et al.

(10) Patent No.: US 12,714,325 B2
(45) Date of Patent: Aug. 25, 2026

(54) SYSTEMS FOR AND METHODS OF PERFORMING GASTROINTESTINAL MANOMETRY

(71) Applicant: Covidien LP, Mansfield, MA (US)

(72) Inventors: Ryan S. Sohlden, Lyons, CO (US); Aria S. A. Thakore, Superior, CO (US); Jennifer Lin, Broomfield, CO (US)

(73) Assignee: Covidien LP, Mansfield, MA (US)

(*) Notice: Subject to any disclaimer, the term of this patent is extended or adjusted under 35 U.S.C. 154(b) by 552 days.

(21) Appl. No.: 18/143,683

(22) Filed: May 5, 2023

(65) Prior Publication Data

US 2023/0355124 A1 Nov. 9, 2023

Related U.S. Application Data

(60) Provisional application No. 63/338,577, filed on May 5, 2022.

(51) Int. Cl.
*A61B 5/03* (2006.01)
*A61B 5/00* (2006.01)

(52) U.S. Cl.
CPC ............ *A61B 5/037* (2013.01); *A61B 5/4205* (2013.01); *A61B 5/6852* (2013.01); *A61B 5/742* (2013.01); *A61B 2562/0247* (2013.01); *A61B 2562/04* (2013.01)

(58) Field of Classification Search
CPC ..... A61B 5/037; A61B 5/4205; A61B 5/6852; A61B 5/742; A61B 5/4233; A61B 5/743; A61B 2562/0247; A61B 2562/04
See application file for complete search history.

(56) References Cited

U.S. PATENT DOCUMENTS 8,790,275 B2 7/2014 Parks et al.
2014/0343415 A1* 11/2014 Hoffman ................ A61B 6/485 600/431
2018/0078195 A1* 3/2018 Sutaria .................... A61M 1/73
(Continued)

FOREIGN PATENT DOCUMENTS

ES 2392641 T3 12/2012

OTHER PUBLICATIONS

Asad Jehangir, et al. "Characterizing Reflux on High Resolution Esophageal Manometry with Impedance." BMC Gastroenterology, vol. 22, No. 1, Mar. 8, 2022, bmcgastroenterol.biomedcentral.com/articles/10.1186/s12876-022-02194-0, https://doi.org/10.1186/s12876-022-02194-0. Accessed Sep. 11, 2025. (Year: 2022).*
(Continued)

*Primary Examiner* — Patrick Fernandes
*Assistant Examiner* — Melissa Jo Montgomery
(74) *Attorney, Agent, or Firm* — Carter, DeLuca & Farrell, LLP

(57) ABSTRACT

A method of assisting a manometry procedure includes recording, by a processor, a plurality of pressure measurements taken by a catheter inserted within a gastrointestinal tract of a patient, determining, by the processor, a pressure pattern based on the plurality of pressure measurements, and determining whether the determined pressure pattern is an acceptable pressure pattern or an unacceptable pressure pattern.

11 Claims, 20 Drawing Sheets

(56) References Cited

U.S. PATENT DOCUMENTS

2021/0113099 A1 4/2021 Rogers et al.

OTHER PUBLICATIONS

Roman S, Gyawali CP, Xiao Y, Pandolfino JE, Kahrilas PJ. The Chicago classification of motility disorders: an update. Gastrointest Endosc Clin N Am. Oct. 2014;24(4):545-61. doi: 10.1016/j.giec. 2014.07.001. Epub Aug. 1, 2014. PMID: 25216902; PMCID: PMC4163199. (Year: 2015).*

W.O.A. Rohof, et al., "Chicago Classification of Esophageal Motility Disorders: Lessons Learned", Curr Gastroenterol Rep (2017), vol. 19, No. 37, pp. 1-6.

* cited by examiner

Achalasia Subtypes

Type I

Type II

Type III 30 mmHg 30 mmHg 30 mmHg mmHg

Esophageal SPAM

Hypotensive Lower Esophageal Sphincter/Hiatus Hernia 292.3s

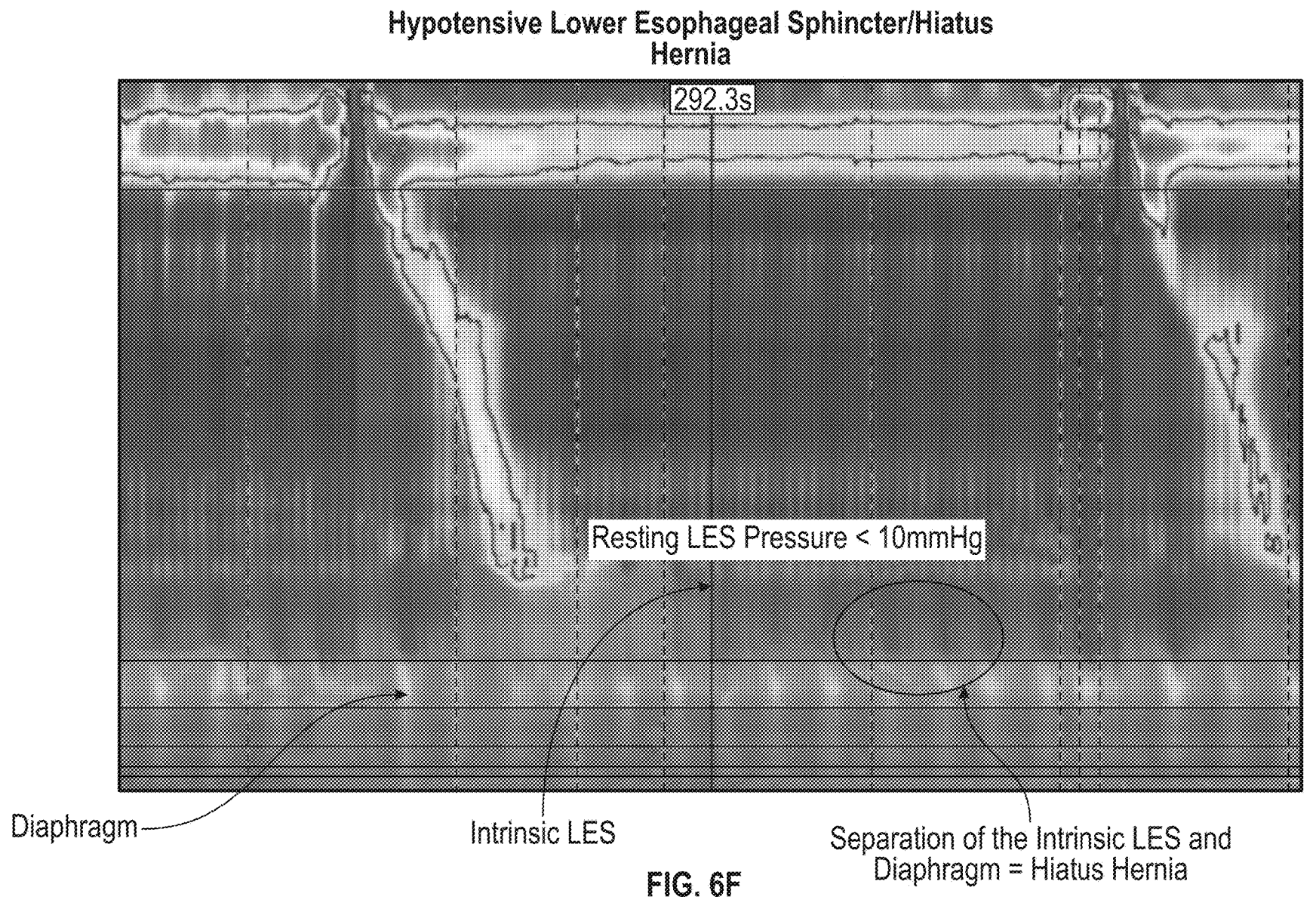

Resting LES Pressure < 10mmHg

Separation of the Intrinsic LES and Diaphragm = Hiatus Hernia

Intrinsic LES

Diaphragm

FIG. 6F

SYSTEMS FOR AND METHODS OF PERFORMING GASTROINTESTINAL MANOMETRY

CROSS-REFERENCE TO RELATED APPLICATIONS

This application claims the benefit of the filing date of provisional U.S. Patent Application No. 63/338,577 filed on May 5, 2022.

FIELD

The present technology is related generally to systems for and methods of performing gastrointestinal manometry.

BACKGROUND

Manometry is the measurement of pressure. Esophageal manometry measures the muscular pressure exerted along the upper GI tract, for example, during peristalsis. Esophageal manometry is used to evaluate the contraction function of the upper GI tract in many situations (e.g., breathing, swallowing food, swallowing liquid, drinking, etc.) and can be useful for diagnosing symptoms that originate in the esophagus, for example, difficulty in swallowing food or liquid, heartburn, and chest pain to determine the cause of the symptoms, for example, dysphasia or achalasia.

A variety of esophageal manometry systems have been used to study pressure along the upper GI tract. Such systems typically include a manometric catheter or probe that is placed in the esophagus of a patient to record pressure and/or impedance data over a period of time using various sensors placed on the catheter. The data is analyzed using analysis software to evaluate causes of, and help diagnose, conditions such as gastric reflux, difficulty swallowing, functional chest pain, achalasia, and hiatal hernia. In aspects, the systems provide high resolution and/or three-dimensional mapping of pressure levels within the tubular organs of the human gastrointestinal tract and, optionally, pressure with impedance levels within the tubular organs of the human upper gastrointestinal tract.

SUMMARY

In accordance with an aspect of the disclosure, a method of assisting a gastrointestinal manometry is provided. The method includes recording a determined pressure pattern including a plurality of pressure measurements taken by a catheter inserted within a gastrointestinal tract of a patient; determining, by a processor, whether the determined pressure pattern is an acceptable pressure pattern or an unacceptable pressure pattern; and notifying a clinician when a threshold number of acceptable pressure patterns is collected.

In aspects, determining whether the determined pressure pattern is the acceptable pressure pattern or the unacceptable pressure pattern may include comparing, by the processor, the determined pressure pattern with known acceptable pressure patterns and known unacceptable pressure patterns.

In aspects, the acceptable pressure pattern may be representative of a proper swallow, and the unacceptable pressure pattern may be representative of a fault condition of the catheter or an improper swallow.

In aspects, the method may further include displaying a tally of a total number of acceptable pressure patterns collected.

In aspects, the method may further include visually and/or audibly alerting the clinician when the determined pressure pattern is determined to be the unacceptable pressure pattern.

In aspects, the method may further include displaying the determined pressure pattern on a display.

In accordance with another aspect of the disclosure, a method of performing gastrointestinal manometry is provided that includes inserting a catheter into a gastrointestinal (GI) tract of a patient; prompting the patient to swallow, whereby a plurality of pressure sensors of the catheter determine a pressure pattern including a respective pressure at a plurality of locations of the GI tract; determining, by a processor, whether the determined pressure pattern is an acceptable pressure pattern or an unacceptable pressure pattern; notifying a clinician when a threshold number of acceptable pressure patterns is collected; and removing the catheter from the patient after the clinician is notified that the threshold number of acceptable pressure patterns is collected.

In accordance with another aspect of the present disclosure, a system for performing gastrointestinal manometry is provided. The system includes a memory having instructions stored thereon, and a processor in communication with the memory. The processor, in response to executing the instructions, is configured to determine whether a determined pressure pattern is an acceptable pressure pattern or an unacceptable pressure pattern by comparing the determined pressure pattern with known acceptable pressure patterns and known unacceptable pressure patterns. The determined pressure pattern includes a respective pressure at a plurality of locations of a GI tract over a period of time, and the known acceptable pressure patterns are representative of a proper swallow, and the known unacceptable pressure patterns are representative of a fault condition of the catheter or an improper swallow.

In aspects, the processor may be further configured to provide a notification when a threshold number of acceptable pressure patterns is collected.

In aspects, the known acceptable pressure patterns and the known unacceptable pressure patterns may be stored in the memory.

In aspects, the system may further include a display, and the processor is further configured to cause the display to display a tally of a total number of acceptable pressure patterns collected.

In aspects, the processor may be further configured to cause the system to provide at least one of a visual or audible alert when the determined pressure pattern is determined to be the unacceptable pressure pattern.

BRIEF DESCRIPTION OF THE DRAWINGS

The accompanying drawings, which are incorporated in and constitute a part of the specification, illustrate aspects of the disclosure and, together with a general description of the disclosure given above as well as the detailed description of the aspects given below, serve to explain the principles of this disclosure, wherein:

FIG. 6A illustrates three temporal displays of pressure patterns each of which being indicative of a subtype of achalasia;

FIG. 6F illustrates a temporal display of a pressure pattern indicative of hypotensive lower esophageal sphincter;

DETAILED DESCRIPTION

As used herein, the term "distal" refers to the portion that is being described which is further from a clinician, while the term "proximal" refers to the portion that is being described which is closer to a clinician. As used herein, the terms parallel and perpendicular are understood to include relative configurations that are substantially parallel and substantially perpendicular up to about +/−10 degrees from true parallel and true perpendicular. Further, to the extent consistent, any of the aspects described herein may be used in conjunction with any or all of the other aspects described herein.

During a manometry procedure, a catheter with pressure sensors is inserted into the patient's nose and passed down the esophagus into the stomach, and in some instances into the intestines. The catheter sensors measure the contractions of the esophageal muscles as the patient swallows. Sensor output is shown on the display including pressure and impedance data points for esophageal, anorectal, and antroduodenal manometry. Clinicians are often worried about the quality of their data during manometry procedures due to the inevitable stress and resulting disruptions to the swallow collection the patient experiences during the procedure.

Accordingly, the present disclosure provides a method of assisting a manometry procedure by identifying and scoring patient swallow patterns to give a clinician greater confidence in their data collection. The method also includes identifying and recording common disruptions to the procedure (e.g., coughing, swallowing at the wrong time, catheter flipping, etc.) so that clinician may react in real-time to any identified disruptions to efficiently collect the necessary quality swallows.

The method includes applying a pattern recognition algorithm (e.g., an artificial intelligence (AI) algorithm) to pattern recognition of events during a manometry procedure. The algorithm differentiates disruptive events (e.g., cough displaying as violent short time interval patterns) from representative swallows (e.g., elongated controlled movement of fluid). In addition, the method includes counting (e.g., using a counter) accumulated representative patterns to determine that the correct number of patterns have been collected for analysis to begin. This improves a clinician's experience by reducing the number of tasks during a manometry procedure, enabling the clinician to detect catheter issues more easily (e.g., flipping), and ensuring the accuracy of the collected data. The method of the present disclosure also improves patient experience by reducing the procedure time by reducing the number of swallows required. These and other aspects of the present disclosure are described in greater detail below.

Figure 1:
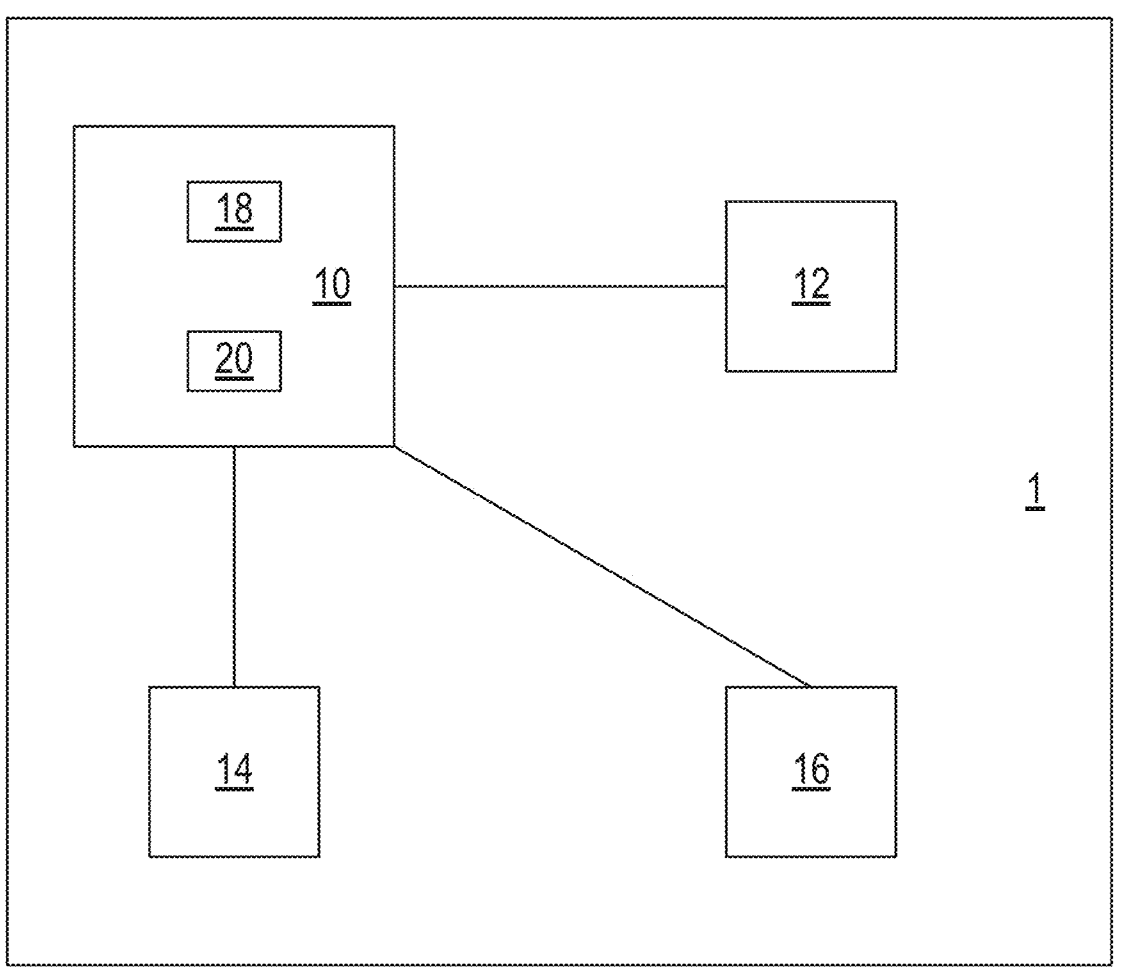
FIG. 1 is a schematic illustration of a manometry system according to aspects of the present disclosure.

With reference to FIG. 1, a system 1 for performing a gastrointestinal manometry generally includes a computer 10, a probe or catheter 12, a user interface(s) 14, and a camera 16. The computer 10 may include any suitable processor 18 operably connected to a memory 20, which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor 18 may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor 18 may be substituted for by using any logic processor (e.g., control circuit) adapted to execute algorithms, calculations, and/or set of instructions described herein.

The memory 20 of the computer 10 has stored thereon instructions, which when executed by the processor 18, cause the system 1 to analyze a pressure pattern, such as, for example, a plurality of pressure measurements taken along a gastrointestinal tract of a patient by the catheter 12 when a patient swallows, that may be presented as waveforms with topographical plots, to determine whether the patient swallow was acceptable. The memory 20 of the computer 10 further has stored thereon a plurality of prerecorded pressure patterns that are known to correspond with an acceptable swallow by a patient (e.g., the pressure patterns shown in FIGS. 6A-6J), and a plurality of prerecorded pressure patterns that are known to correspond with an unacceptable swallow by a patient (e.g., the pressure patterns shown in FIGS. 7A-7E). The swallow by a patient may produce pressure data or a pressure pattern that is equivalent to or substantially similar to one of the prerecorded pressure patterns that correspond with a normal swallow of a patient. A normal swallow of a patient may include a swallow that indicates a diagnosable motility disorder or a swallow not indicative of a diagnosable motility disorder. As such, the processor 18, by matching the measured pressure pattern with one of the prerecorded/known pressure patterns, may determine that the measured pressure pattern is acceptable.

Alternatively, the swallow by the patient may produce pressure data or a pressure pattern (e.g., pressure measurements over time) that is equivalent to or substantially similar to one of the prerecorded pressure patterns that correspond with a fault condition, such as, for example, a cough of a patient, a swallow by a patient at an improper time, a flipping of the catheter, a dislodgment of the catheter, etc. In this instance, the processor 18, by matching the measured pressure pattern with one of the prerecorded/known pressure patterns associated with one of the above fault conditions, the processor 18 may determine that the measured pressure pattern is unacceptable.

Figure 2:
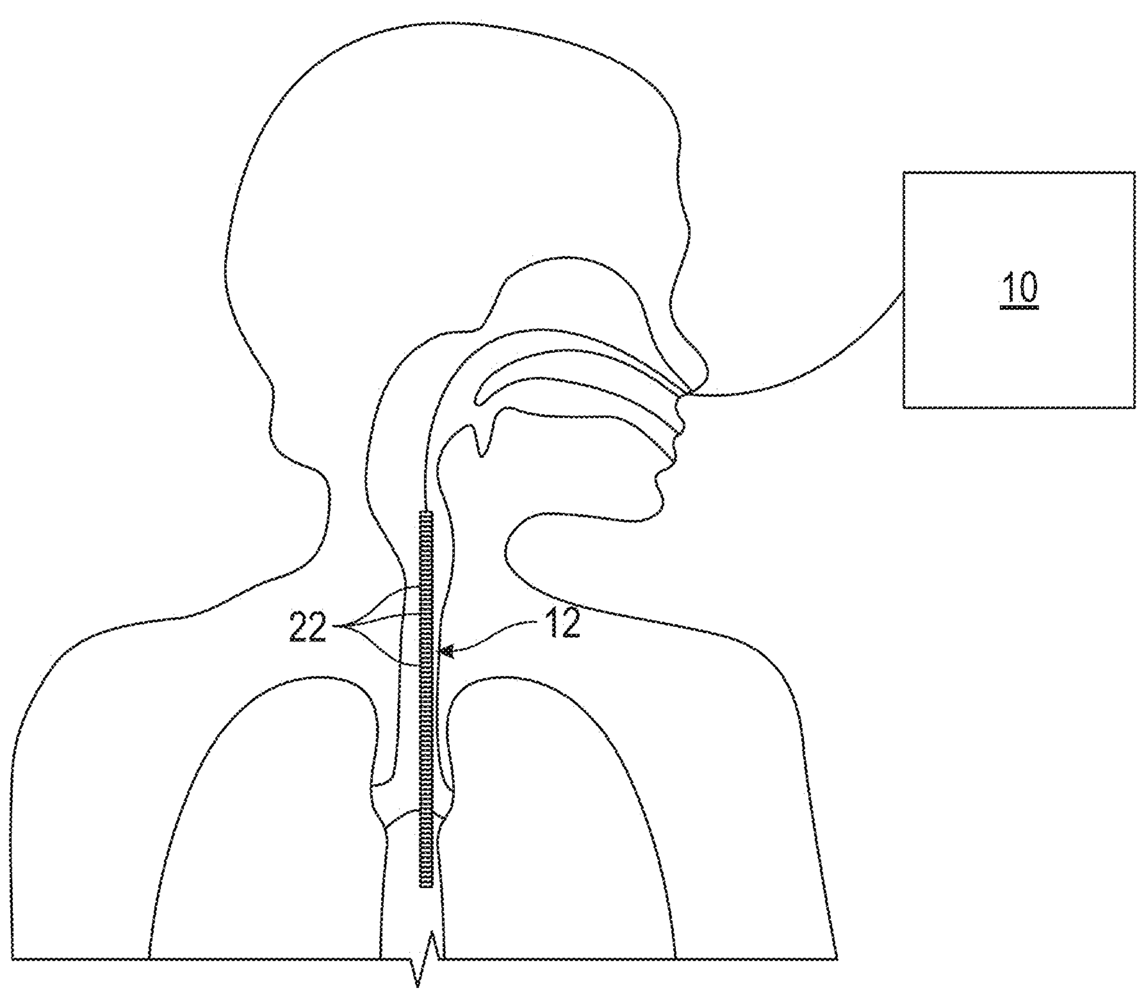
FIG. 2 is a front view illustrating a catheter of the system of FIG. 1 inserted in a GI tract.

With reference to FIG. 2, the catheter or probe 12 has a plurality of sensors 22 attached thereto and spaced from one another along a length of the catheter 12. The sensors 22 may be any suitable type of sensor, such as, for example, pressure sensors such as a capacitive pressure sensor, a solid state sensor, or the like. The sensors 22 may be configured to measure pressure in response to contact with tissue, such as, for example, tissue of a GI tract. The sensors 22 may be configured to sense a variety of physical properties, for example, pressure, pH, temperature, voltage, tissue impedance, another physical property, or any combination thereof.

Figure 3:
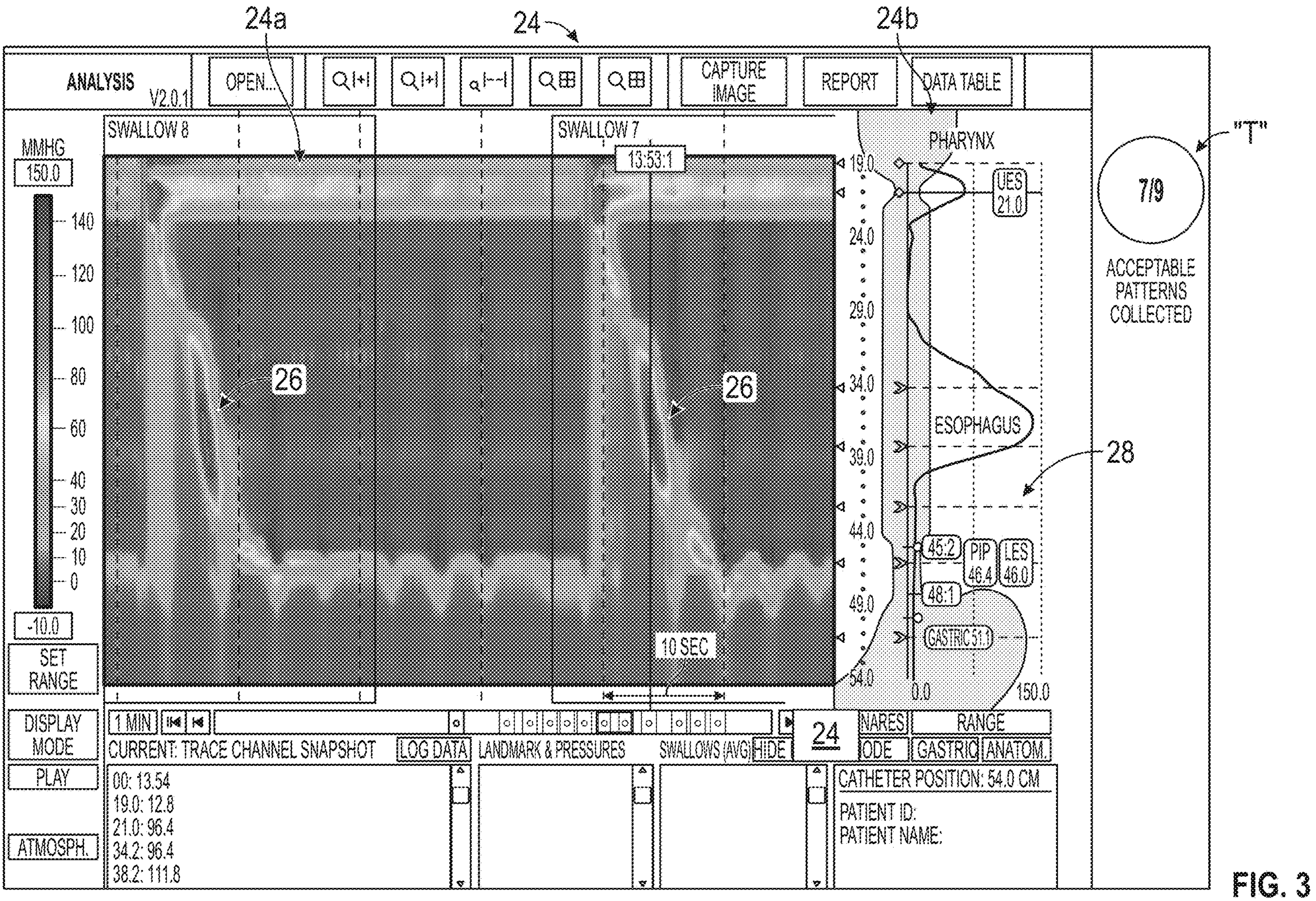
FIG. 3 is screen shot illustrating an example of a user interface display displaying current pressure measurement data.

During a manometry procedure, the catheter 12 is inserted in a patient's GI tract and the patient is asked to swallow, whereby the sensors 22 measure the pressure at discrete locations along the GI tract and convey the pressure measurements to the processor 18 (FIG. 1) in the form of pressure data or a pressure pattern. The processor 18 displays the pressure pattern on a user interface display 24 of the user interface 14, as shown in FIG. 3. In aspects, the camera 16 may capture video of the GI tract and sync with the pressure measurements by the sensors 22 to generate a 3D map of the GI tract during swallowing overlayed with the pressure data.

With reference to FIG. 3, the user interface display 24 includes two displays for providing visual representations of the pressure patterns to a user: a temporal display 24*a* and a snapshot display 24*b*. Temporal display 24*a* may be a display having both a temporal dimension and a spatial dimension, and may contain a temporal representation, e.g., a contour plot 26 for each swallow measurement. Snapshot display 24*b* may be a display having spatial dimension, including a spatial visual axis, and may contain a spatial representation, e.g., a profile plot 28 that illustrates the pressure data/pattern (or other data such as impedance data) for a particular time, as opposed to over a period of time.

Contour plot 26 may be displayed on a left-side of temporal display 24*a*. Contour plot 26 may represent to a user the pressure data derived from the pressure information measured by the sensors 22 at a plurality of positions over time. In the example shown in FIG. 3, the plurality of positions for which the pressure data are represented to the user may represent positions within the esophageal tract at which sensors 22 are positioned. In this example, the horizontal dimension of contour plot 26 represents time and the vertical dimension represents a first spatial dimension (e.g., within an organism).

For more details regarding the pressure data and its manner of display, reference may be made to U.S. Pat. No. 8,790,275, the entire contents of which are incorporated by reference herein.

Figure 4:
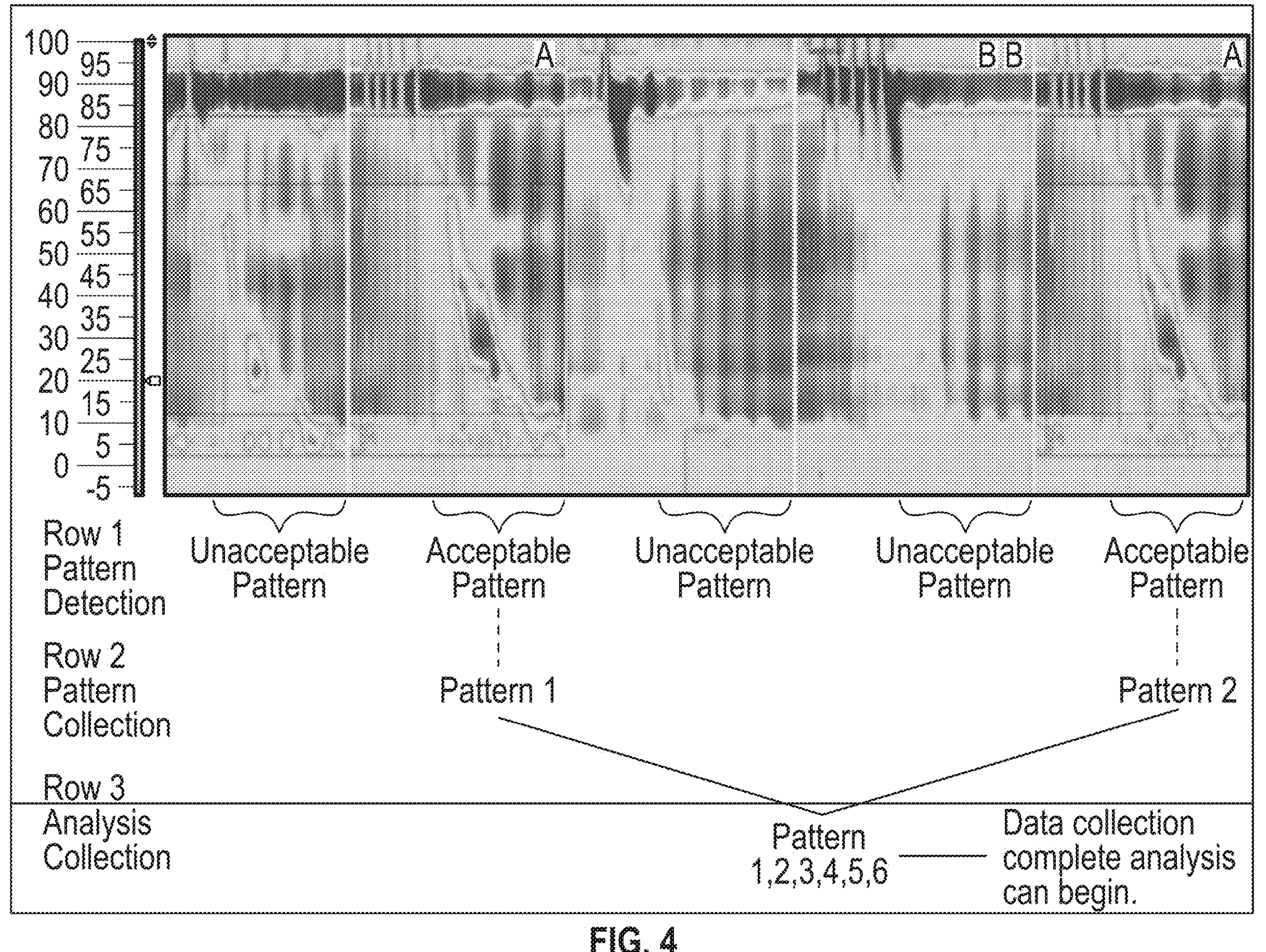
FIG. 4 is a screen shot of another user interface display displaying past pressure measurement data.
Figure 5:
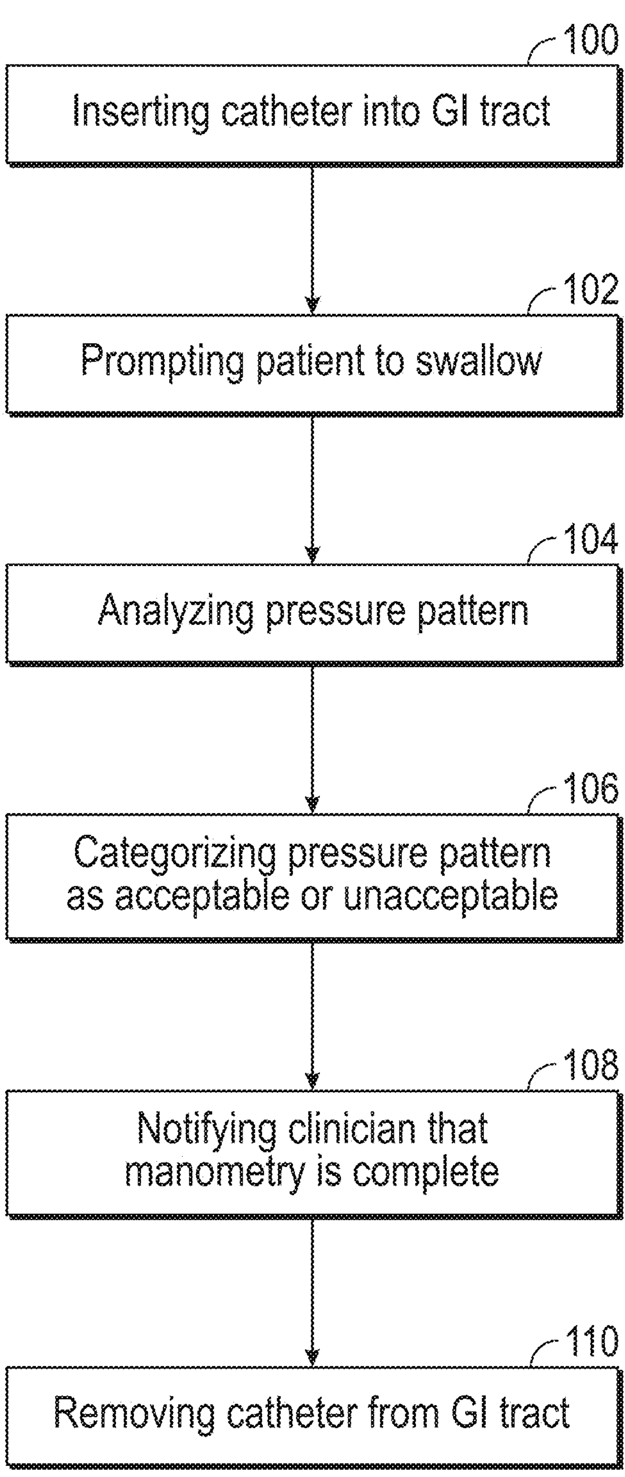
FIG. 5 is a flow diagram of a method for performing a manometry procedure.

In operation, with reference to FIGS. 3-5, to perform a manometry procedure utilizing the system 1 of the present disclosure, at step 100, the catheter 12 is inserted into through a nasal cavity into the upper GI tract such that at least a portion of the probe resides in a pharynx, UES, esophagus, LES, and stomach of the patient, as shown in FIG. 2. In aspects, the catheter 12 may be positioned in any of a variety of combination of organs, including tubular organs, other than within the upper GI tract. For example, the catheter 12 may be inserted in the duodenum, the small bowel, the bile duct, the colon, the Sphincter of Oddi, the urethra, the anus or the rectum.

With the catheter 12 in position within the upper GI tract, at step 102, the clinician may prompt the patient to swallow, whereby the pressure sensors 22 (FIG. 2) of the catheter 12, and in some instances the impedance sensors (not explicitly shown) of the catheter 12, measure a respective pressure at a plurality of locations of the GI tract and coveys the measurements to the processor 18 as a determined pressure pattern. At step 104, the processor 18 (FIG. 1), based on the instructions stored on the memory 20, analyzes the determined pressure pattern of the swallow, and at step 106, the processor 18 determines whether the determined pressure pattern is an acceptable pressure pattern or an unacceptable pressure pattern.

Figure 6A:
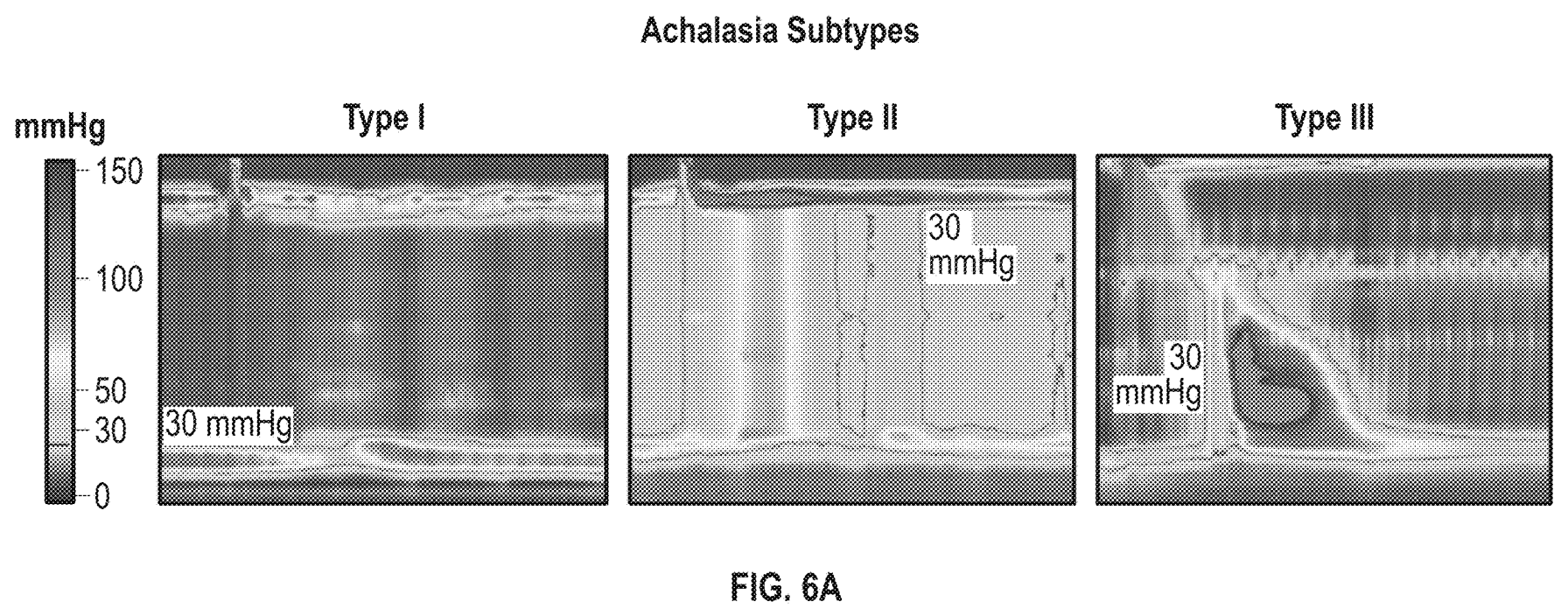
Figure 6B:
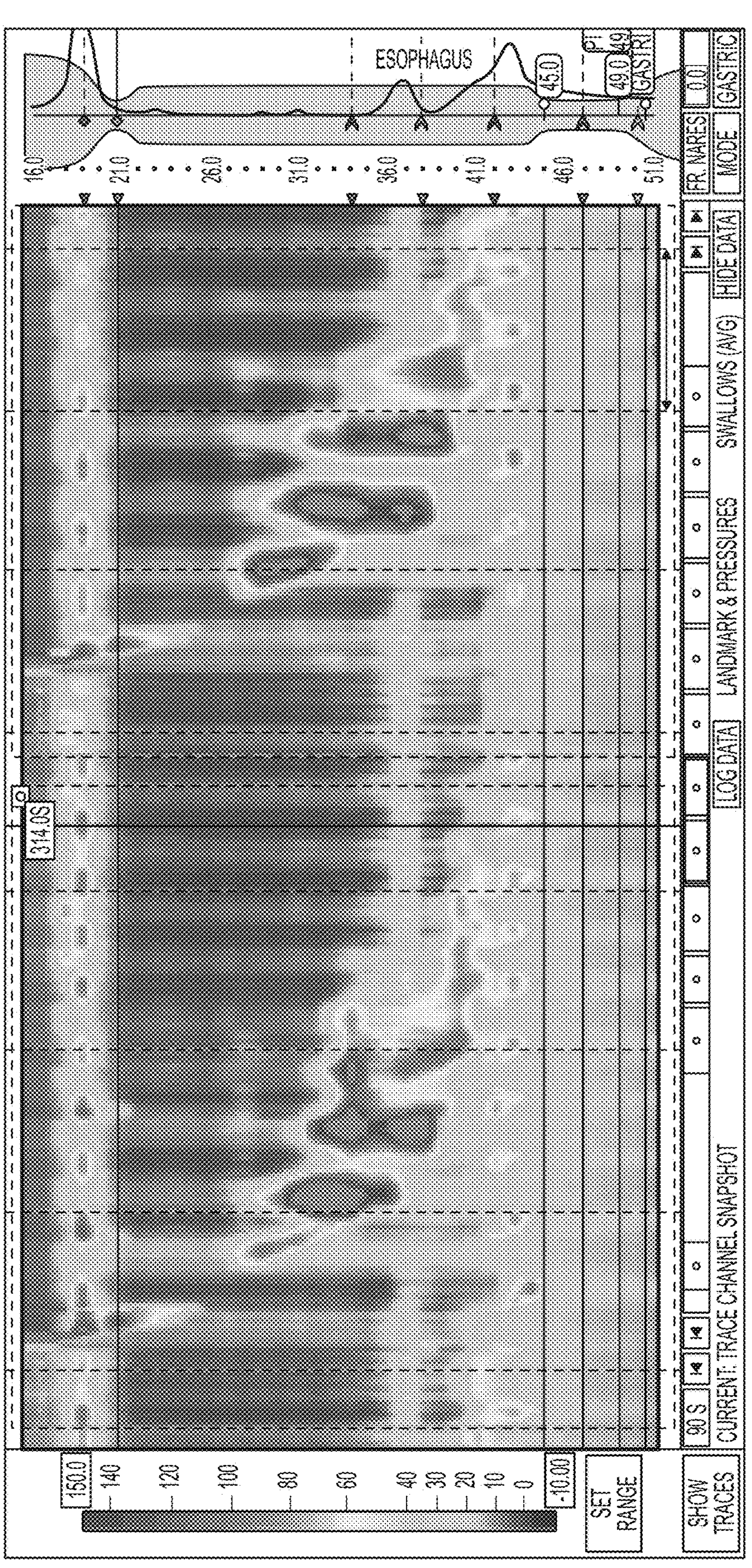
FIG. 6B illustrates a temporal display and a snapshot display of a pressure pattern indicative of an esophageal spasm.
Figure 6C:
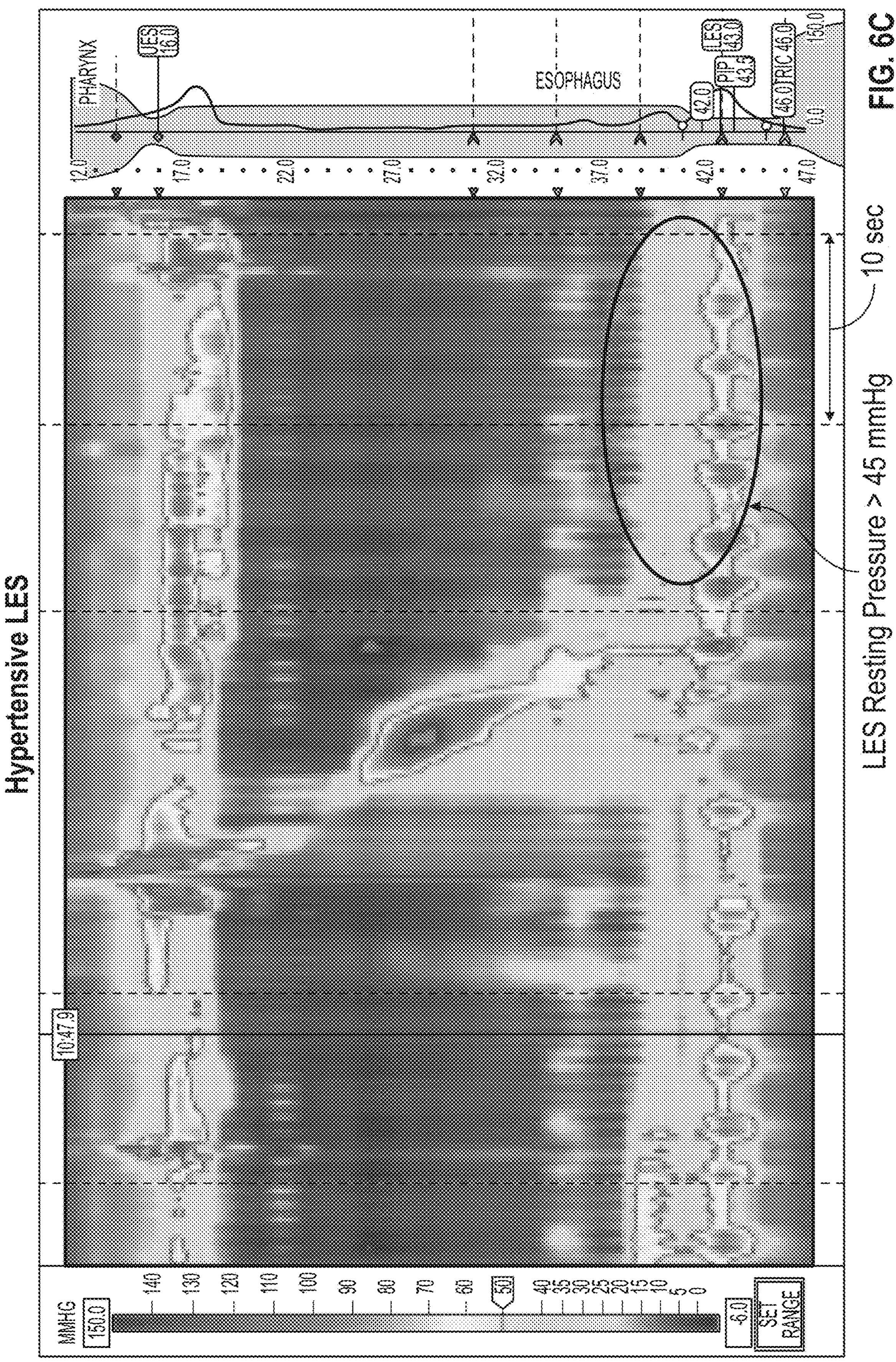
FIG. 6C illustrates a temporal display and a snapshot display of a pressure pattern indicative of a hypertensive lower esophageal sphincter ("LES")
Figure 6D:
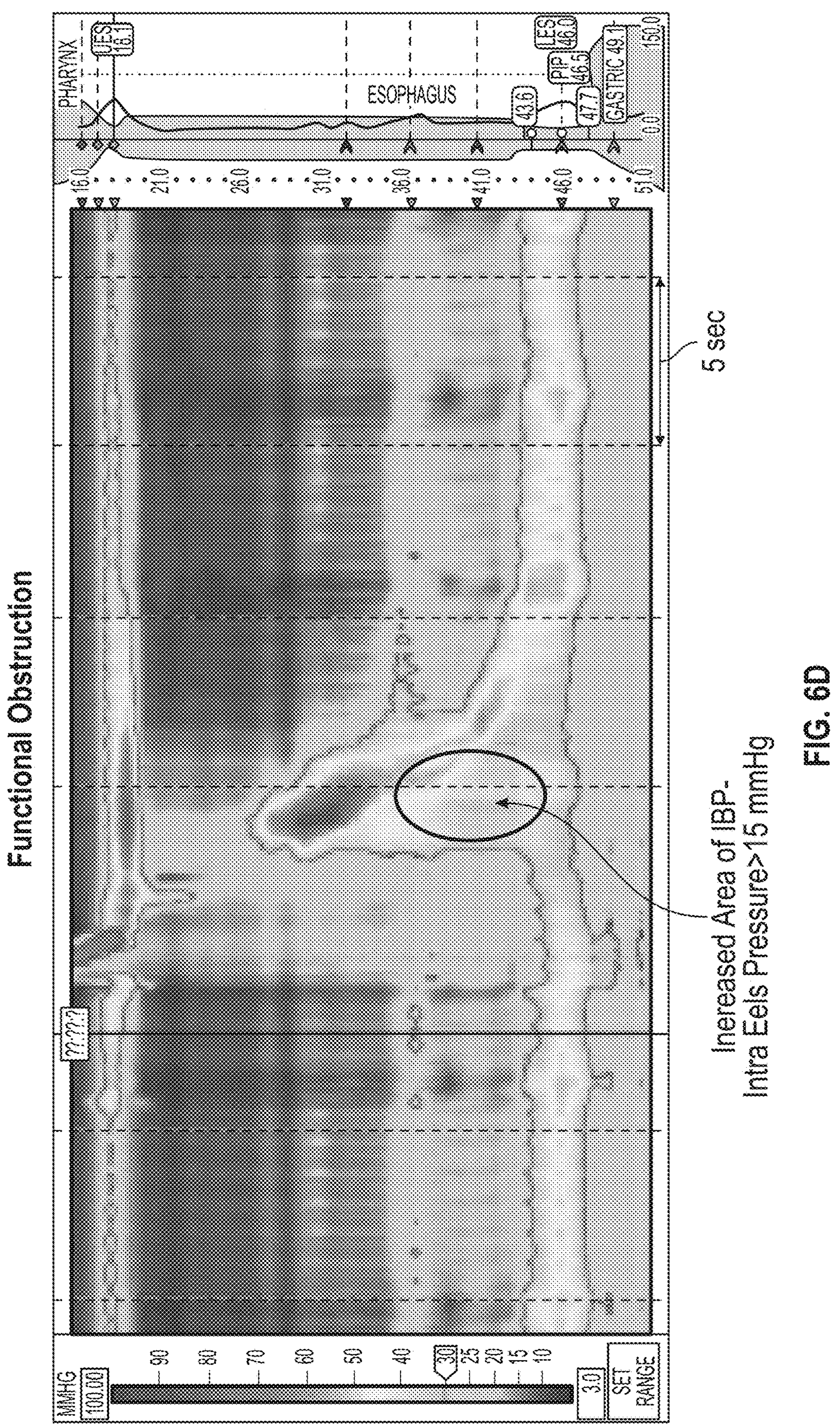
FIG. 6D illustrates a temporal display and a snapshot display of a pressure pattern indicative of a functional obstruction.
Figure 6E:
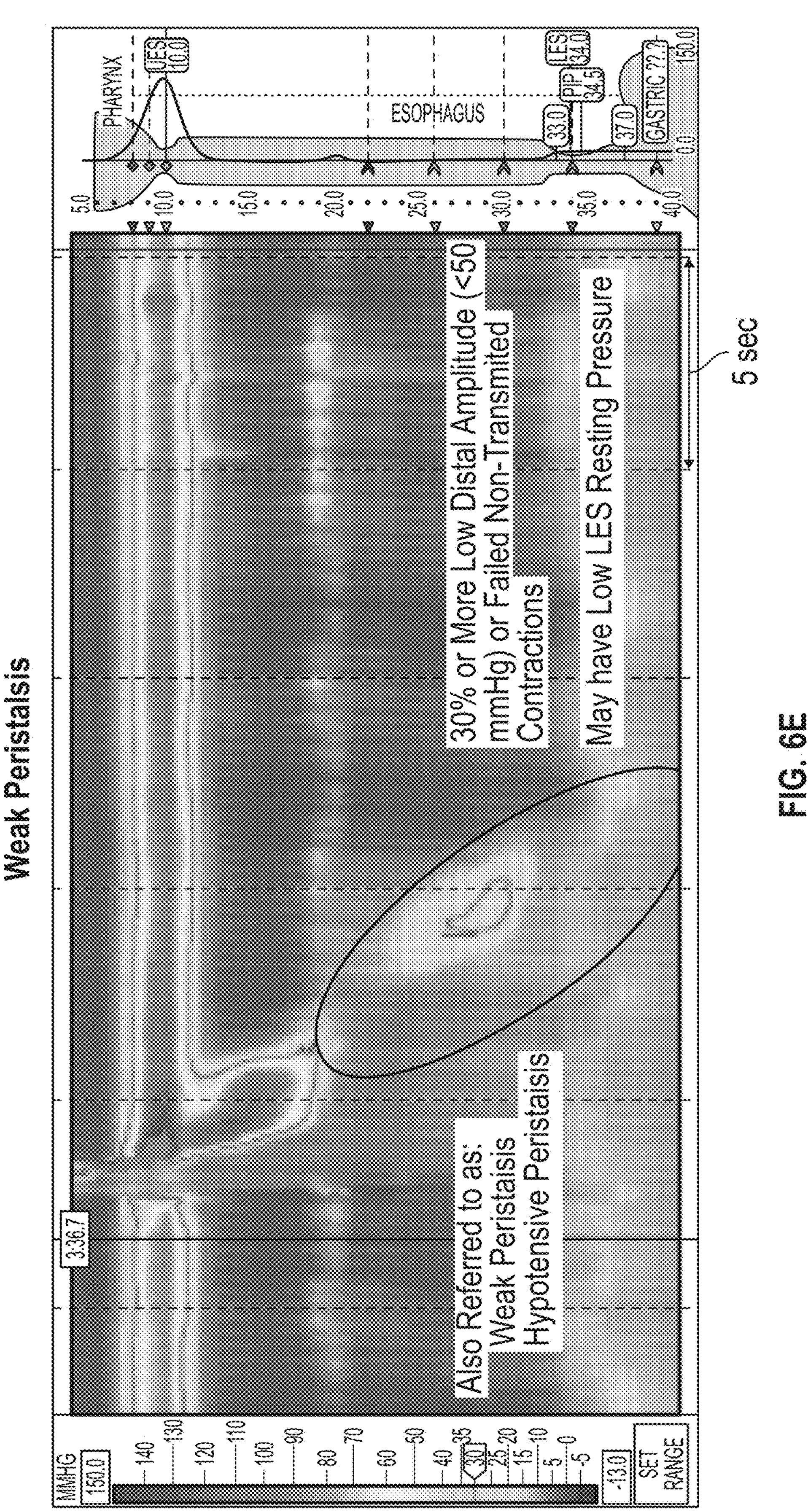
FIG. 6E illustrates a temporal display and a snapshot display of a pressure pattern indicative of a weak peristalsis (i.e., hypotensive peristalsis)
Figure 6G:
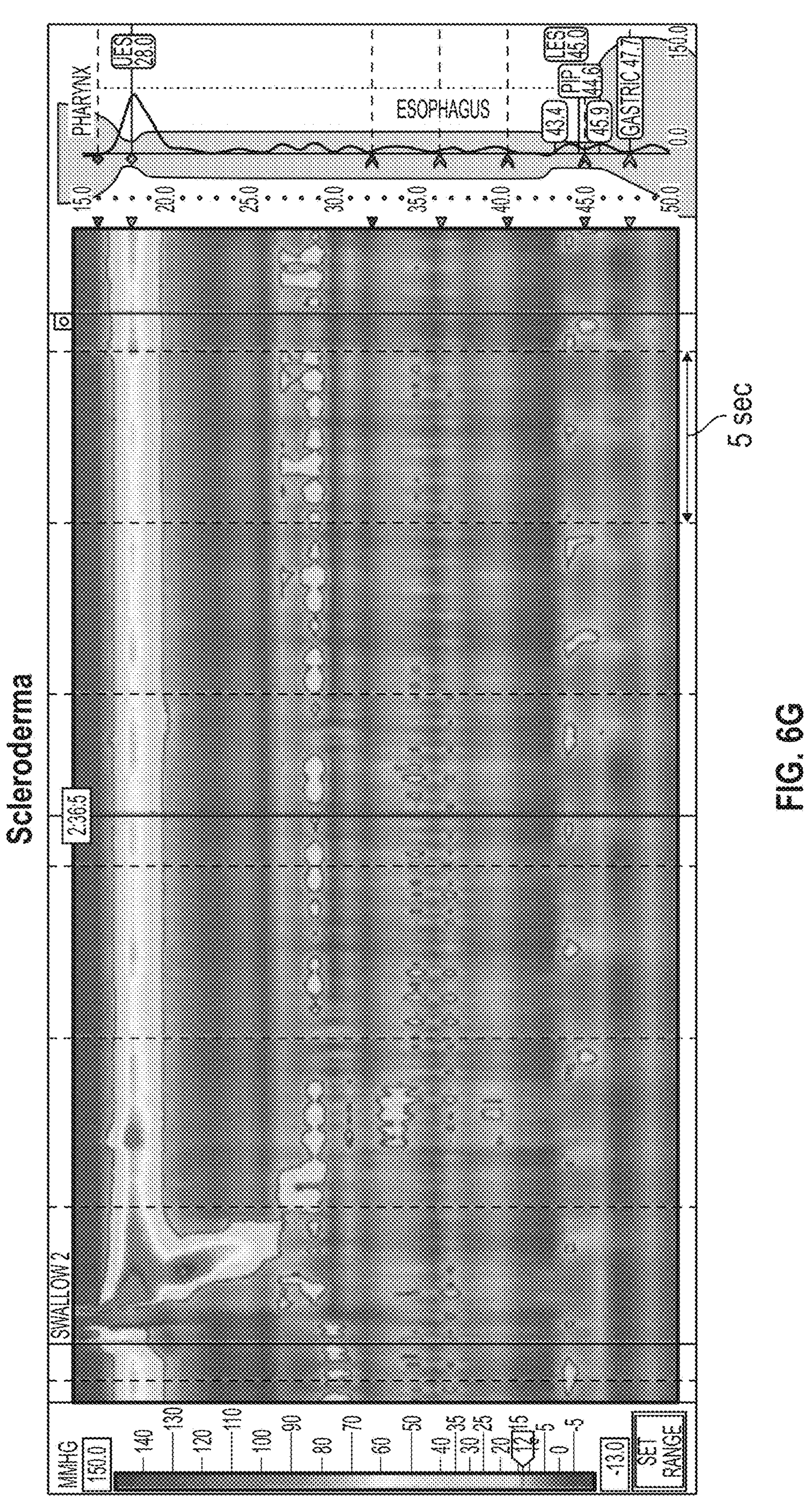
FIG. 6G illustrates a temporal display and a snapshot display of a pressure pattern indicative of a scleroderma.
Figure 6H:
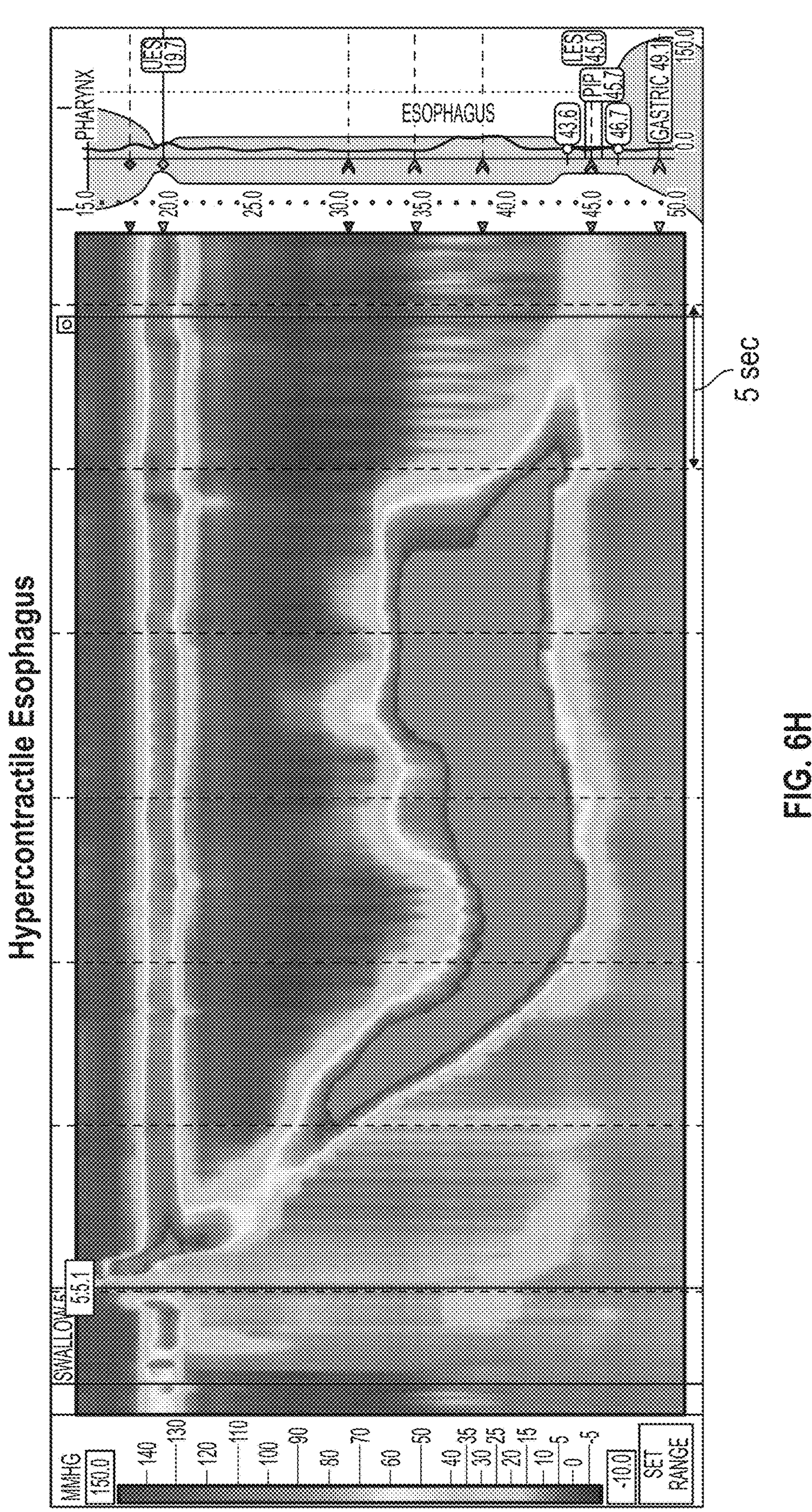
FIG. 6H illustrates a temporal display and a snapshot display of a pressure pattern indicative of a hypercontractile esophagus.
Figure 6I:
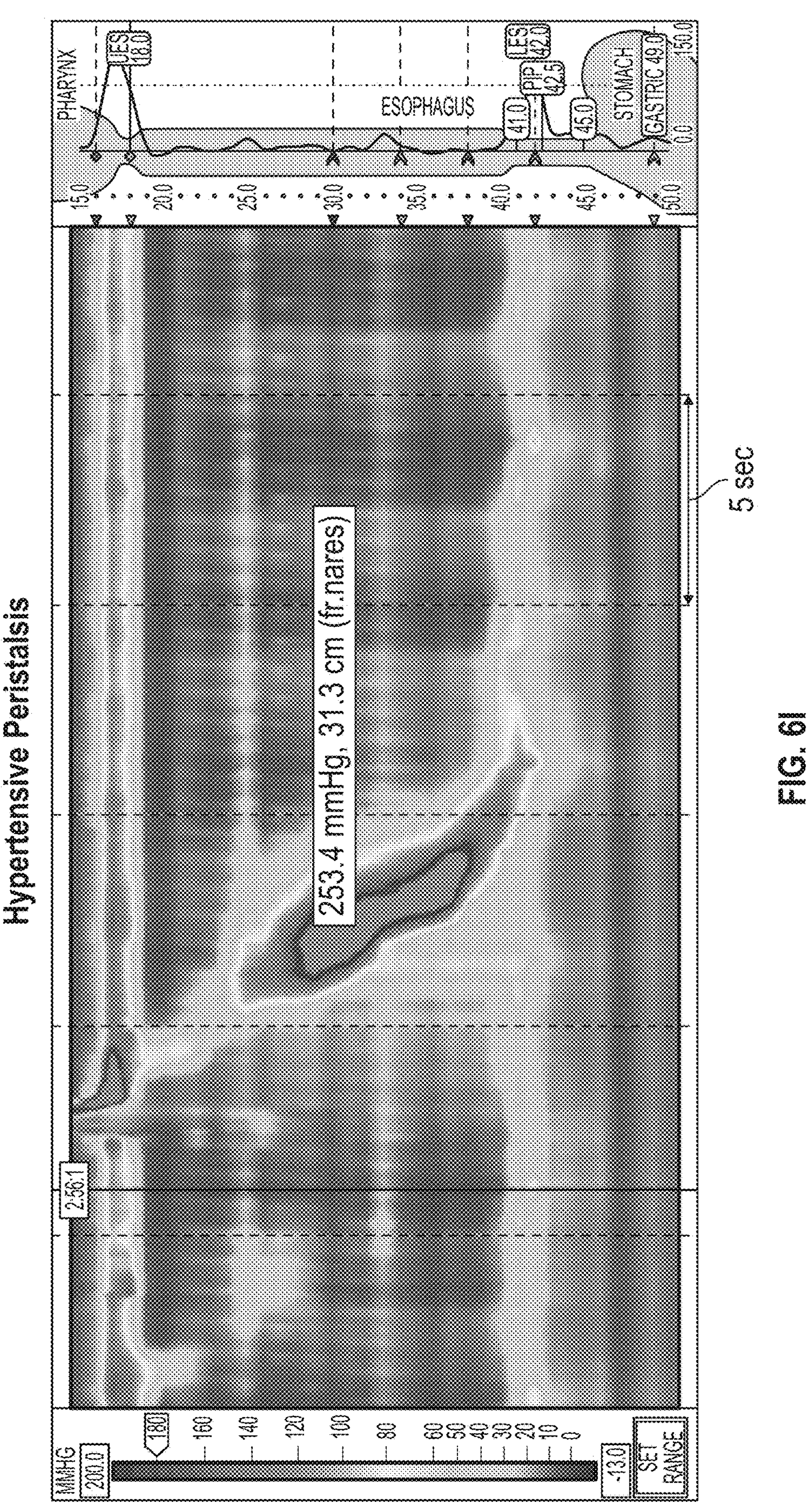
FIG. 6I illustrates a temporal display and a snapshot display of a pressure pattern indicative of a hypertensive peristalsis.
Figure 6J:
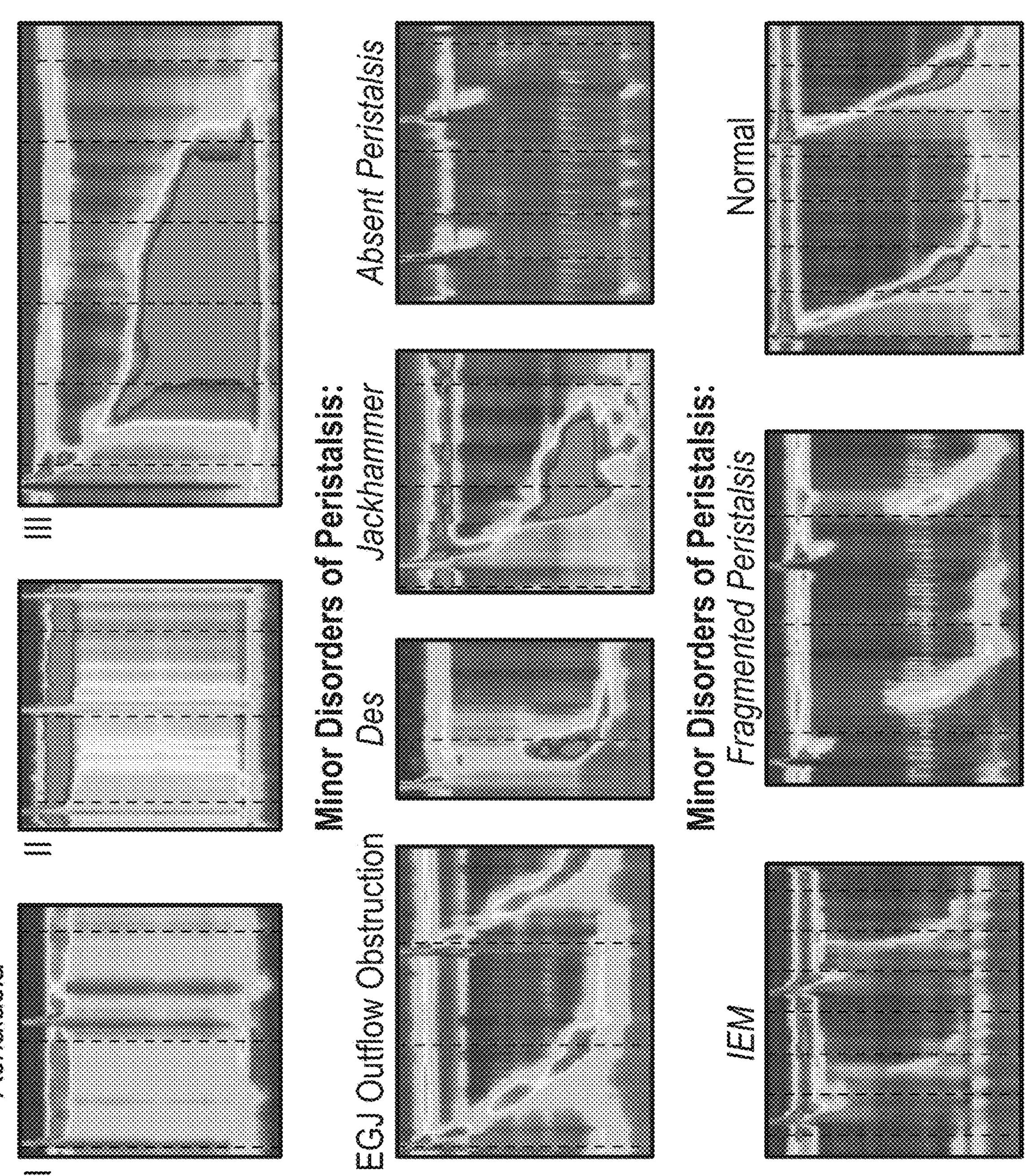
FIG. 6J illustrates three rows of temporal displays of various acceptable pressure patterns.

For example, the processor 18 may compare the determined pressure pattern with the known acceptable pressure patterns and the known unacceptable pressure patterns stored in the memory 20. Exemplary acceptable pressure patterns are shown in FIGS. 6A-6J. FIG. 6A illustrates three temporal displays of pressure patterns each of which being indicative of a subtype of achalasia. FIG. 6B illustrates a temporal display and a snapshot display of a pressure pattern indicative of an esophageal spasm. FIG. 6C illustrates a temporal display and a snapshot display of a pressure pattern indicative of hypertensive lower esophageal sphincter ("LES") as evidenced by the resting pressure being greater than 45 mmHg. FIG. 6D illustrates a temporal display and a snapshot display of a pressure pattern indicative of a functional obstruction as evidenced by an increased area of intra-bolus pressure being greater than 15 mmHg. FIG. 6E illustrates a temporal display and a snapshot display of a pressure pattern indicative of a weak peristalsis (i.e., hypotensive peristalsis) as evidenced by a low LES resting posture. FIG. 6F illustrates a temporal display of a pressure pattern indicative of hypotensive lower esophageal sphincter (i.e., hiatus hernia) as evidenced by a resting LES pressure less than 10 mmHg and a separation of the intrinsic LES and diaphragm. FIG. 6G illustrates a temporal display and a snapshot display of a pressure pattern indicative of a scleroderma. FIG. 6H illustrates a temporal display and a snapshot display of a pressure pattern indicative of a hypercontractile esophagus. FIG. 6I illustrates a temporal display and a snapshot display of a pressure pattern indicative of a hypertensive peristalsis. FIG. 6J illustrates in the first row, temporal displays of pressure patterns indicative of three subtypes of achalasia, in the second row, temporal displays of pressure patterns indicative of (from left to right) esophagogastric junction ("EGJ") outflow obstruction, diffuse esophageal spasm ("DES"), jackhammer esophagus, absent peristalsis, and in the third row (from left to right), temporal displays of pressure patterns indicative of ineffective esophageal motility ("IEM"), fragmented peristalsis, and normal peristalsis.

Figure 7A:
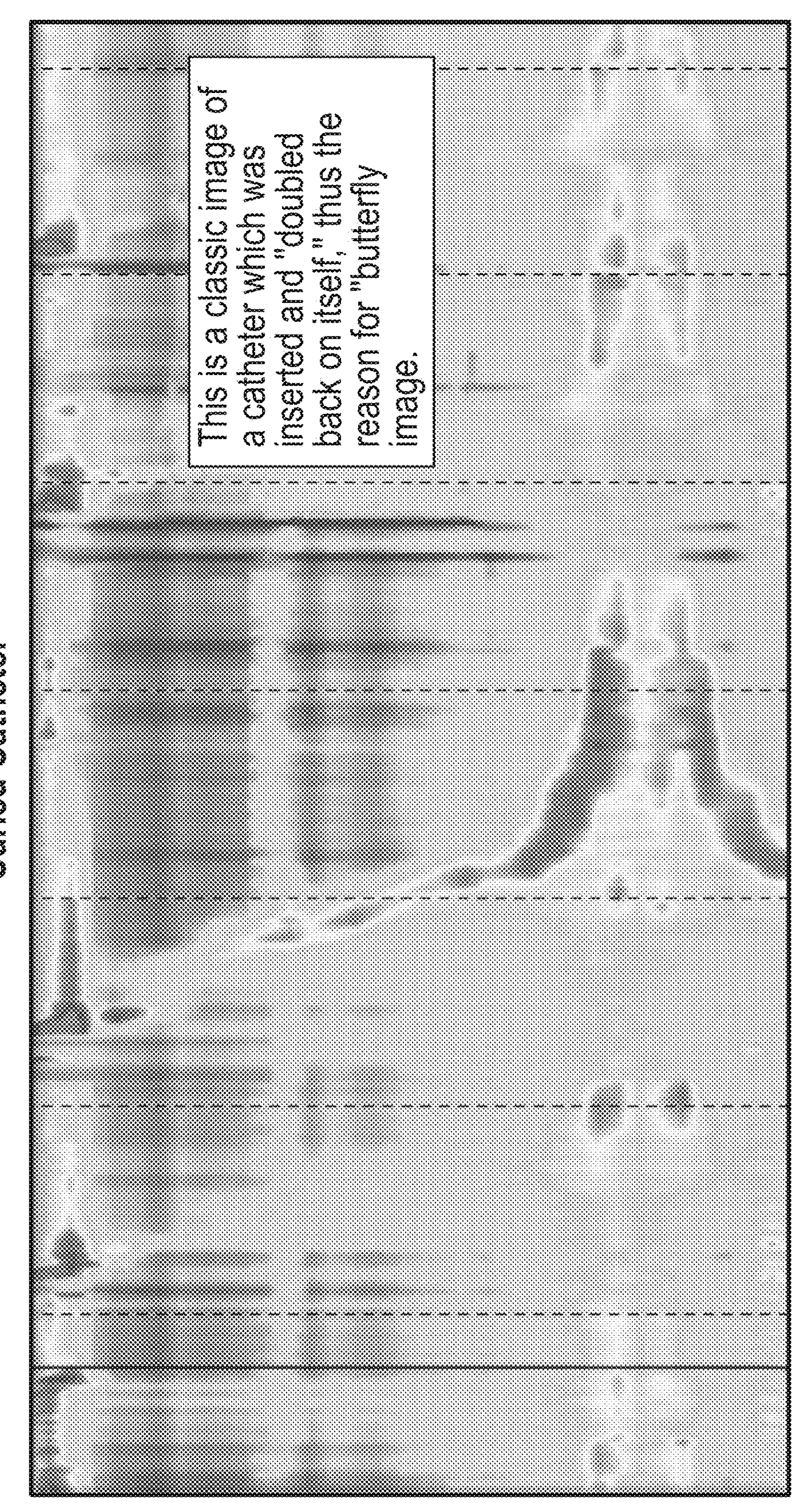
FIG. 7A illustrates a temporal display of a pressure pattern indicative of a curled catheter.
Figure 7B:
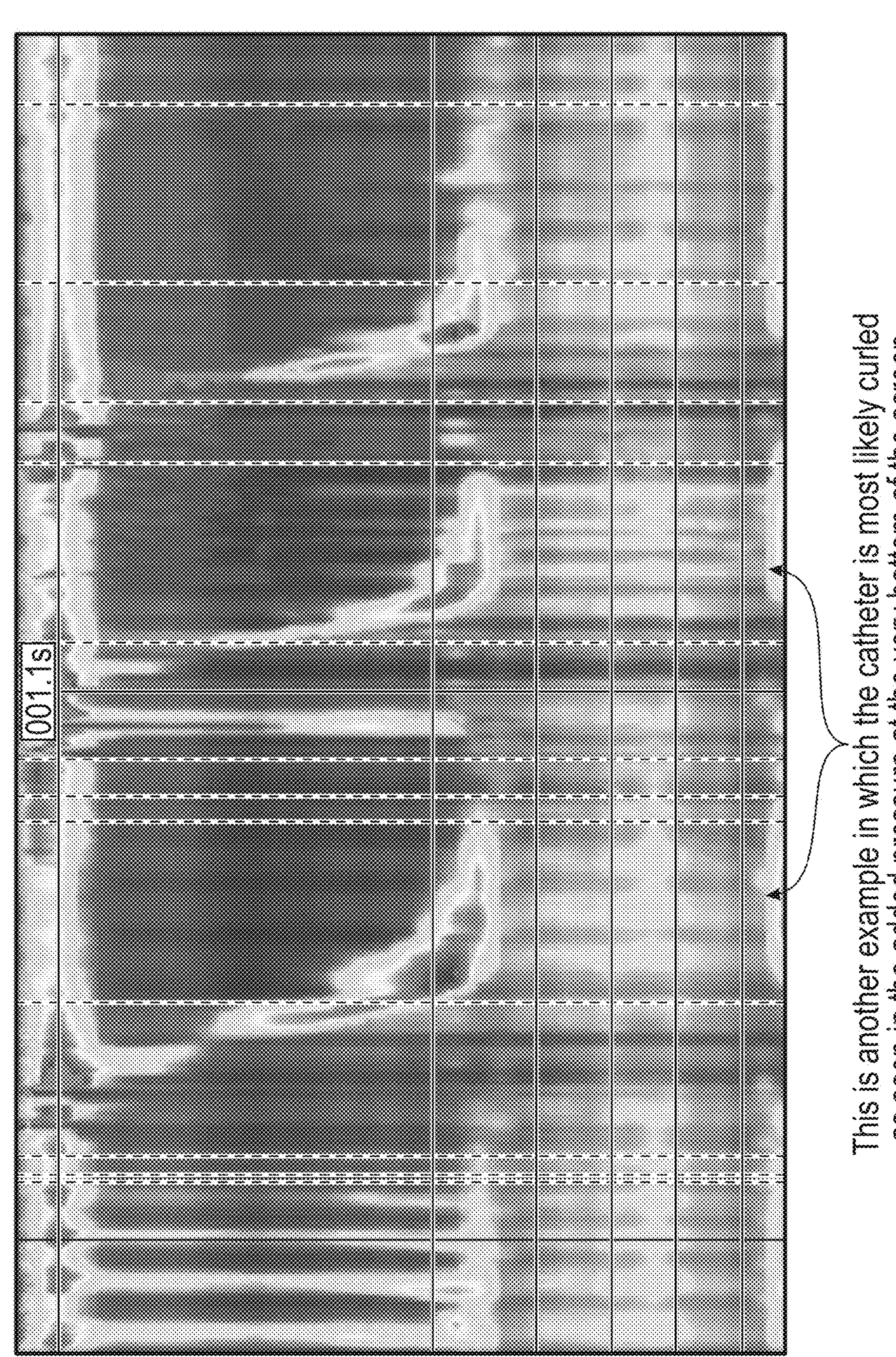
FIG. 7B illustrates a temporal display of a pressure pattern indicative of a folded catheter.
Figure 7C:
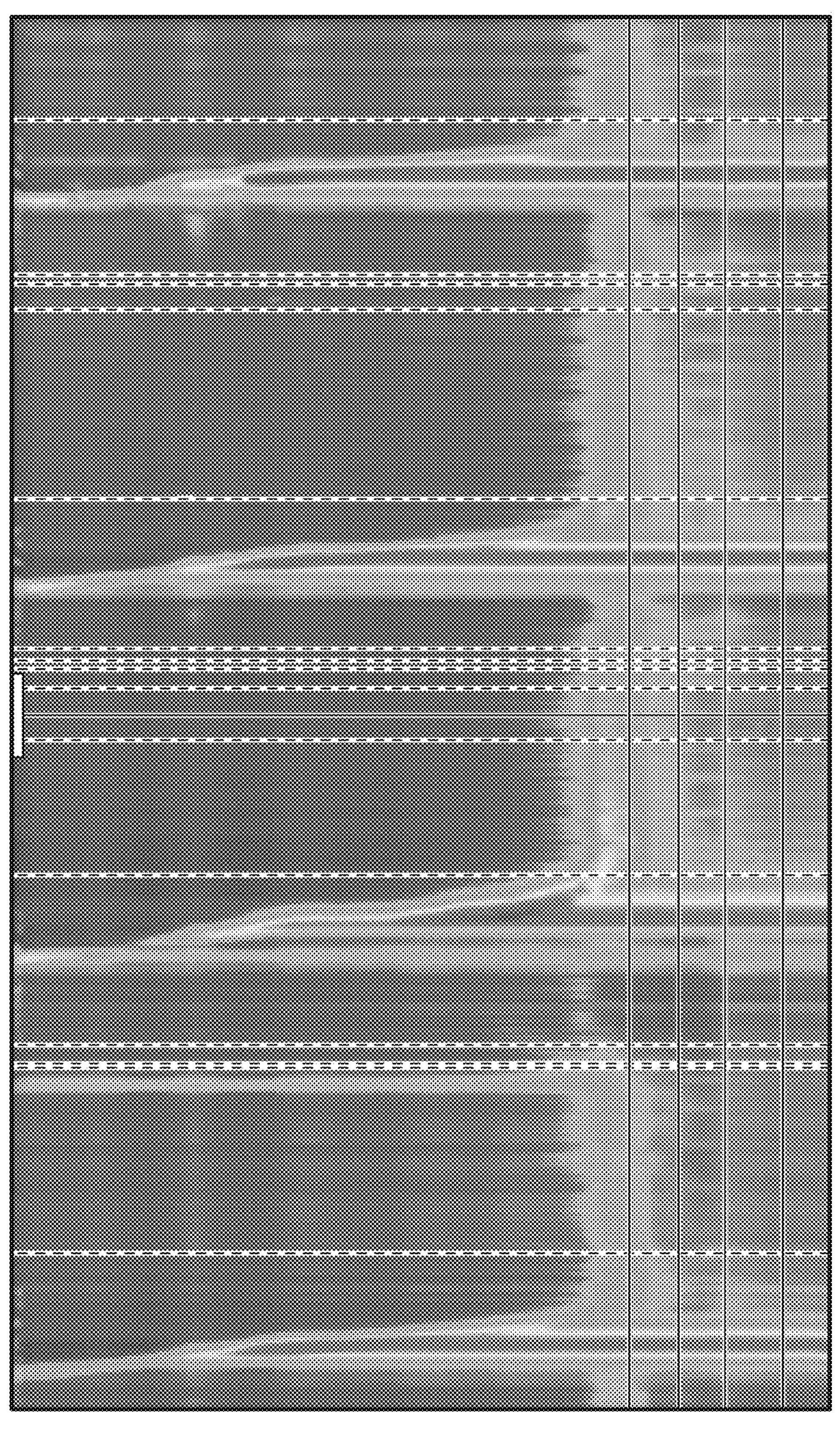
FIG. 7C illustrates a temporal display of a pressure pattern indicative of air being trapped in the catheter.
Figure 7D:
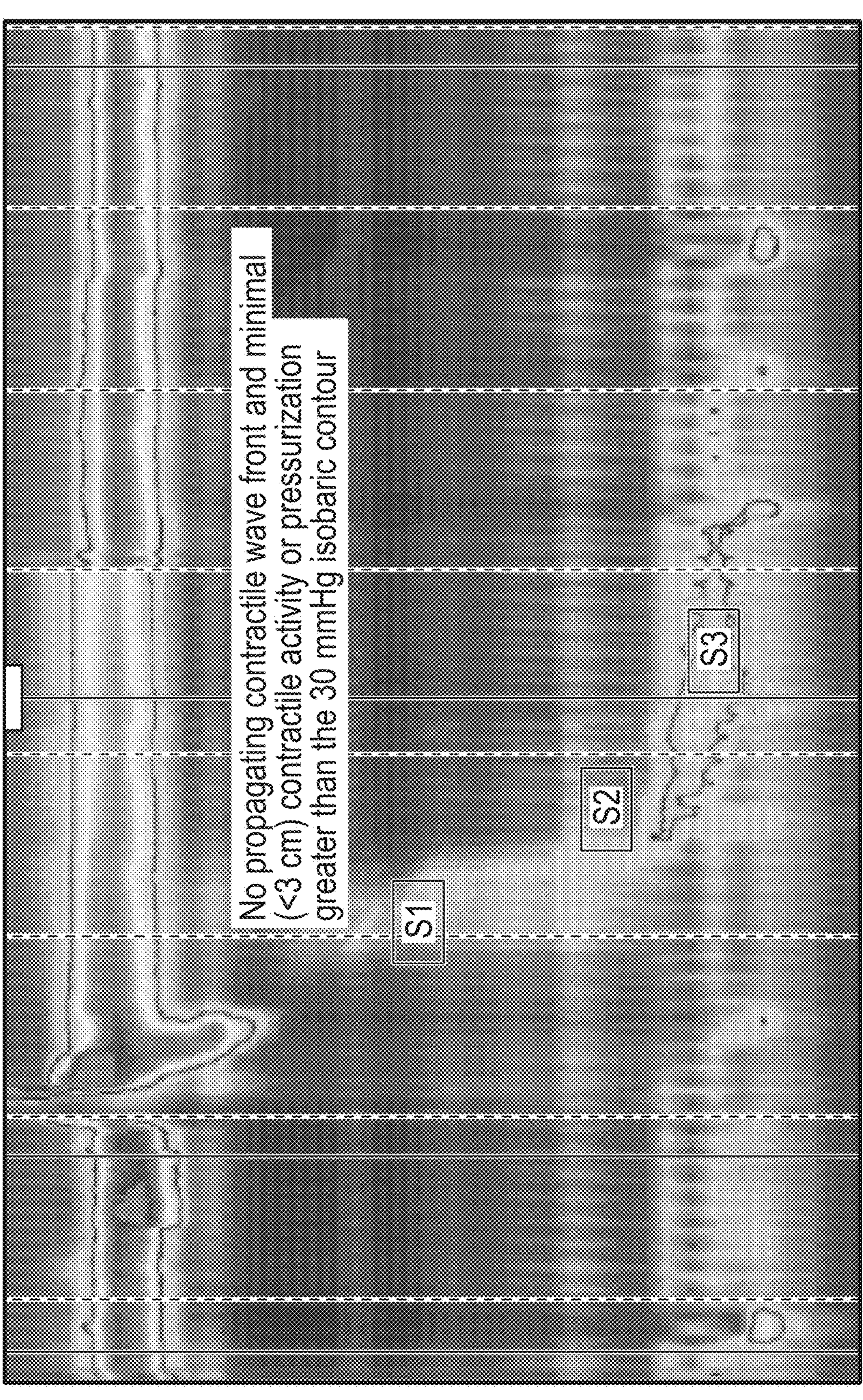
FIG. 7D illustrates a temporal display of a pressure pattern indicative of a failed swallow by a patient.
Figure 7E:
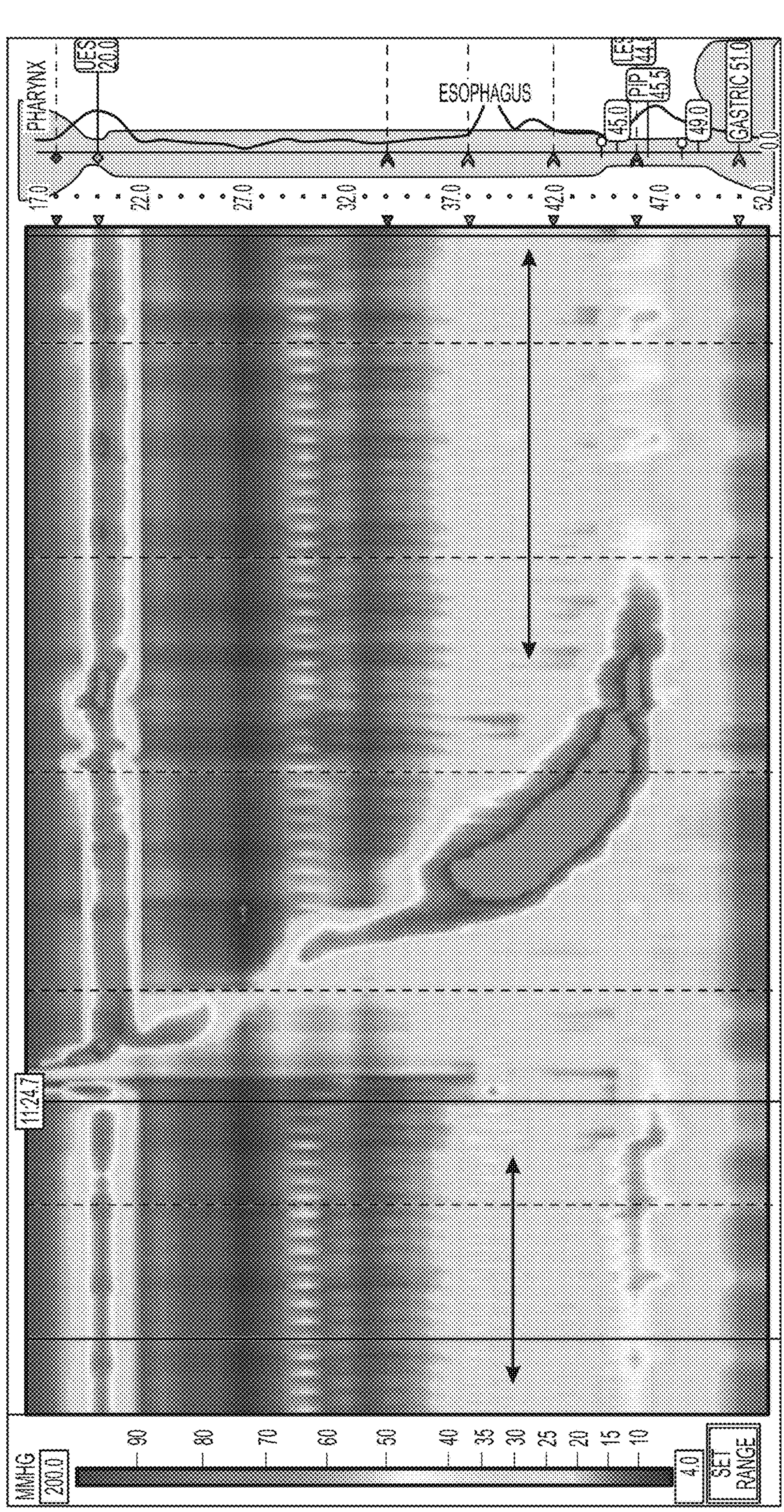
FIG. 7E illustrates a temporal display and a snapshot display of a pressure pattern indicative of a vascular artifact.

Exemplary unacceptable pressure patterns are shown in FIGS. 7A-7E. FIG. 7A illustrates a temporal display of a pressure pattern indicative of a curled catheter (e.g., doubled back on itself) as evidenced by the "butterfly" pattern. FIG. 7B illustrates a temporal display of a pressure pattern indicative of a folded (e.g., curled) catheter as evidenced by added pressure at the bottom of the display. FIG. 7C illustrates a temporal display of a pressure pattern indicative of air being trapped in the catheter. FIG. 7D illustrates a temporal display of a pressure pattern indicative of a failed swallow by a patient as evidenced by there being no propagating contractile wave front and minimal (e.g., less than 3 cm) contractile activity or pressurization greater than the 30 mmHg isobaric contour. FIG. 7E illustrates a temporal display and a snapshot display of a pressure pattern indicative of a vascular artifact.

With continued reference to FIGS. 3-5, if the processor 18 matches the determined pressure pattern with one of the known unacceptable pressure patterns, for example, one of the pressure patterns shown in FIGS. 7A-7E, the processor 18 categorizes the swallow as unacceptable, as shown in Row 1 of FIG. 4. For example, the processor 18, utilizing the pattern recognition algorithm stored in the memory 20, recognizes that the determined pressure pattern matches (e.g., looks substantially similar to) the "butterfly" pattern shown in FIG. 7A. As such, the processor 18 determines that the catheter 12 was in a curled condition when the pressure data was being recorded and marks the swallow as being unacceptable. It is contemplated that the processor 18 may superimpose the determined pressure pattern over each of the known pressure patterns to find a match. Other suitable techniques for the processor 18 to determine a match are also contemplated, such as, for example, comparing critical data points of the determined pressure pattern with critical data points of each of the known patterns.

The processor 18 may notify the clinician, via an audible or visual alert, that the swallow was unacceptable. In addition, the processor 18 may be configured to notify the clinician of the particular fault condition responsible for the swallow being categorized as unacceptable, and in some aspects provide an indication of the cause of the fault condition and/or provide guidance to the clinician on how to correct the fault condition. For example, the system 10 may indicate that the swallow was determined to be a cough, or the catheter 12 was flipped, dislodged, or otherwise improperly positioned, or the like. The clinician may then take appropriate action to correct the fault condition from occurring for the subsequent swallow. The processor 18 may store the unacceptable pressure pattern in the memory 18 or discard the unacceptable pressure pattern.

If the processor 18 matches the determined pressure pattern with a known acceptable pressure pattern stored in the memory 20, for example, one of the pressure patterns shown in FIGS. 6A-6J, the processor 18 categorizes the swallow as acceptable, as shown in Row 1 of FIG. 4. For example, the processor 18, utilizing the pattern recognition algorithm stored in the memory 20, recognizes that the determined pressure pattern matches (e.g., looks substantially similar to) one or both of the patterns shown in the temporal display or the snapshot display of FIG. 6B. As such, the processor 18 determines that the measured pressure pattern is indicative of an esophageal spasm. The processor 18 marks the measurement as being acceptable and may then notify the clinician, via an audible or visual alert, that the swallow was acceptable. In addition, the processor 18 indicates in Row 2 of the display (FIG. 4) that the measured pattern is collected. As shown in FIG. 3, a tally "T" of the total number of acceptable pressure patterns collected is displayed. The processor 18, after determining that the measured pressure pattern is acceptable, adds to the tally "T" shown in FIG. 3 so that the clinician has a visual cue of the progress of the manometry procedure.

In addition to the processor 18 classifying the measured pressure pattern as being acceptable or unacceptable, the processor 18 determines a confidence score associated with the determined classification based on the degree to which the measured pressure pattern matches the known pressure pattern stored in the memory 20. For a determined classification of a measured pressure pattern to count towards the number of acceptable swallows, the algorithm stored in the memory 20 has a defined threshold for a sufficient confidence rating. If the defined threshold is met, the algorithm counts the acceptable patterns with a high confidence score.

For low confidence score events, the algorithm may use a general label (e.g., "Inconclusive Swallow" or "Undetermined Event"). A threshold will be used to identify low confidence events. The software will prompt a user for their input to define the low confidence events. The user interface is configured to allow a user to define the type of pattern (e.g., acceptable or unacceptable.). The user may also further tag an event with a description, such as, for example, cough, choke, incomplete swallow, equipment error, etc. The algorithm counts the events with an initial low confidence score that have been determined to be "acceptable patterns" through user input. The algorithm improves over time through machine learning by asking the user to review post-procedure to confirm algorithm classification.

The manometry procedure is continued until a threshold number (e.g., about 10) of acceptable pressure patterns is collected. Upon reaching the threshold number of acceptable pressure patterns, at step 108, the processor 18 notifies the clinician that further swallows by the patient are not necessary. For example, the system 1 may cause the tally "T" to blink, change color, or expand, or provide an audible alert that the manometry procedure is completed. As shown in Row 3 of FIG. 4, the processor 18 may then begin to analyze the collected acceptable pressure patterns. At step 110, the catheter 12 is removed from the patient after the clinician is notified that the threshold number of acceptable pressure patterns is collected.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

What is claimed is:

1. A method of assisting a gastrointestinal manometry, the method comprising:

recording, from a plurality of pressure sensors spaced along a length of a manometry catheter inserted within a gastrointestinal tract of a patient during a swallow, a determined pressure pattern including a plurality of pressure measurements corresponding to respective locations along the gastrointestinal tract;

comparing, by a processor executing instructions stored in a memory, the determined pressure pattern with a set of prerecorded gastrointestinal manometry pressure patterns stored in the memory, the set including patterns representative of proper swallows and patterns representative of catheter fault conditions or improper swallows;

determining, by the processor, whether the determined pressure pattern is an acceptable pressure pattern or an unacceptable pressure pattern based on the comparison; and notifying, by the processor, a clinician when a tally of acceptable pressure patterns determined by the processor reaches a threshold number of acceptable pressure patterns;

removing the manometry catheter from the patient in response to the notification that the threshold number of acceptable pressure patterns determined by the processor has been collected;

wherein determining whether the determined pressure pattern is the acceptable pressure pattern or the unacceptable pressure pattern further includes determining, by the processor, a confidence score associated with determining whether the determined pressure pattern is acceptable or unacceptable based on a degree to which the determined pressure pattern matches a prerecorded gastrointestinal manometry pressure pattern stored in the memory, and wherein the processor counts the determined pressure pattern toward the tally of acceptable pressure patterns only when the confidence score satisfies a defined confidence threshold.

2. The method according to claim 1, further comprising displaying the tally of acceptable pressure patterns determined by the processor.

3. The method according to claim 1, further comprising at least one of visually or audibly alerting the clinician when the determined pressure pattern is determined to be the unacceptable pressure pattern.

4. The method according to claim 1, further comprising displaying the determined pressure pattern on a display.

5. A method of performing gastrointestinal manometry, the method comprising:

inserting a manometry catheter into a gastrointestinal (GI) tract of a patient such that a plurality of pressure sensors spaced along a length of the manometry catheter are positioned at respective locations along the gastrointestinal tract;

prompting the patient to swallow, whereby a plurality of pressure sensors of the manometry catheter determine a pressure pattern including a respective pressure at a plurality of locations of the GI tract over a period of time;

comparing, by a processor executing instructions stored in a memory, the determined pressure pattern with a set of prerecorded gastrointestinal manometry pressure patterns including patterns representative of proper swallows and patterns representative of catheter fault conditions or improper swallows, and determining whether the determined pressure pattern is an acceptable pressure pattern or an unacceptable pressure pattern based on the comparison;

in response to the determined pressure pattern being the unacceptable pressure pattern, repeating the prompting step to obtain an additional swallow for analysis while the manometry catheter remains inserted in the gastrointestinal tract;

updating, by the processor, a tally of acceptable pressure patterns determined by the processor during the gastrointestinal manometry;

notifying a clinician that a threshold number of acceptable pressure patterns determined by the processor has been collected; and removing the manometry catheter from the patient in response to the notification that the threshold number of acceptable pressure patterns determined by the processor has been collected;

wherein determining whether the determined pressure pattern is the acceptable pressure pattern or the unacceptable pressure pattern further includes determining, by the processor, a confidence score associated with determining whether the determined pressure pattern is acceptable or unacceptable based on a degree to which the determined pressure pattern matches a prerecorded gastrointestinal manometry pressure pattern stored in the memory, and wherein the processor counts the determined pressure pattern toward the tally of acceptable pressure patterns only when the confidence score satisfies a defined confidence threshold.

6. The method according to claim 5, further comprising displaying the tally of acceptable pressure patterns determined by the processor.

7. The method according to claim 5, further comprising at least one of visually or audibly alerting the clinician when the determined pressure pattern is determined to be the unacceptable pressure pattern.

8. The method according to claim 5, further comprising displaying the determined pressure pattern on a display.

9. The method according to claim 1, further comprising, when the confidence score is below a low confidence threshold, labeling the determined pressure pattern with a general label and prompting a user for input to classify the determined pressure pattern as acceptable or unacceptable, and wherein the processor counts the determined pressure pattern toward the tally of acceptable pressure patterns based on the user input.

10. The method according to claim 5, further comprising, in response to the determined pressure pattern being the unacceptable pressure pattern, notifying the clinician, via an audible or visual alert, that the swallow was unacceptable and notifying the clinician of a fault condition associated with the swallow being categorized as unacceptable.

11. The method according to claim 5, further comprising, in response to the determined pressure pattern being the unacceptable pressure pattern, storing the unacceptable pressure pattern in the memory or discarding the unacceptable pressure pattern.

* * * * *